United States Patent [19]

Patterson

[11] Patent Number: 5,652,191
[45] Date of Patent: Jul. 29, 1997

[54] PALLADIUM CATALYST SYSTEMS FOR SELECTIVE HYDROGENATION OF DIENES

[75] Inventor: Robert T. Patterson, Baton Rouge, La.

[73] Assignee: DSM Copolymer, Inc., Baton Rouge, La.

[21] Appl. No.: 528,117

[22] Filed: Sep. 14, 1995

Related U.S. Application Data

[62] Division of Ser. No. 310,935, Sep. 22, 1994, Pat. No. 5,475,121, which is a continuation of Ser. No. 042,604, Apr. 2, 1993, abandoned, which is a continuation of Ser. No. 555,043, Jul. 19, 1990, abandoned.

[51] Int. Cl.$^6$ ............................................. B01J 31/00
[52] U.S. Cl. ............................. 502/162; 502/172; 556/6; 556/136; 556/137
[58] Field of Search ........................ 502/162, 172; 556/6, 136, 137

[56] References Cited

U.S. PATENT DOCUMENTS 4,048,093  9/1977  Knifton ...................... 252/414

OTHER PUBLICATIONS

"Palladium–Catalyzed Desulfonylative Coupling of Aryl-solfonyl Chlorides. . . ." Miura, at al, Tetrahedron Lett. (1989), 30(8), 975–6.

"Catalytic Activity of Palladium Metallic Complexes. . . ", Scharf, et al, Izu. Akad. Nauk SSSR, Ser. Khim. (1984), (10), 2384–6.

*Primary Examiner*—Bernard Lipman
*Attorney, Agent, or Firm*—Dressler, Rockey, Milnamow & Katz, Ltd.

[57] ABSTRACT

A catalyst precursor is provided that is useful in the selective hydrogenation of olefinic unsaturation in polymers or copolymers. The precursor comprises a palladium salt that is complexed with a complexing agent selected from the gronp consisting of organic phosphates, dialkylidene acetones, and tetraalkyl ammonium hydroxides. The catalyst precursor may be nsed in batch, step-wise addition, or continuous systems.

3 Claims, No Drawings

PALLADIUM CATALYST SYSTEMS FOR SELECTIVE HYDROGENATION OF DIENES

This is a divisional of application Ser. No. 08/310,935 filed on Sep. 22, 1994, now U.S. Pat. No. 5,475,121, which is a continuation of application Ser. No. 08/042,604 filed on Apr. 2, 1993, now abandoned, which is a continuation of application Ser. No. 07/555,043 filed on Jul. 19, 1990, now abandoned.

The present invention relates to catalyst precursors for homogeneous catalytic systems used to selectively hydrogenate olefinic unsaturation in diene polymers and copolymers. More specifically, the invention relates to the use of colloidal palladim (O) catalysts to selectively hydrogenate olefinic unsaturation in polymers and copolymers.

Hydrogenation of one such copolymer, nitrile rubber (acrylonitrile-butadiene copolymer) results in a product that is resistant to oils, ozone and sour gases, while maintaining a high service temperature on the order of 300°–350° F. As a result, such compositions find particular utility in automotive applications in which formed rubber products are exposed to adverse environments and sustained temperatures of 300° F. or more.

These rubbers are superior in such applications to EPDM compositions, which have similar service temperatures but exhibit poor oil resistance. Fluoro elastomers, which have sufficiently high service temperatures and which exhibit the requisite resistance to oils and sour gases, are significantly more expensive than nitrile rubber and offer inferior elasticity.

Thus, it is desirable to produce a hydrogenated nitrile rubber composition having the advantageous mechanical and resistance properties described above.

It is known in the art that certain noble metal catalysts may be employed to selectively hydrogenate olefinic unsaturation in nitrile rubber and other diene polymers and copolymers to produce desirable properties in the rubber. Catalysts employing salts of platinum, ruthenium, rhodium, iridium and palladium have variously demonstrated their utility in heterogeneous and homogeneous forms.

Numerous supported catalyst systems incorporating those and other metals have been described in the literature. These heterogeneous systems typically involve the deposition of the metal upon an inorganic or organic carrier, such as silica, carbon black, titanium dioxide or diatomaceous earth. Alternatively, solutions of salts or oxides of these metals are impregnated in carrier particles, followed by reduction to the metallic state.

Homogeneous systems, including colloidal systems in which the suspended solid particles are of sufficiently small particle size that they behave like a one-phase system, present a number of advantages over similar heterogeneous systems. In general, homogeneous catalysts offer greater selectivity than heterogeneous systems, and faster rates of reaction at comparable catalyst concentrations since mass transport will not become rate limiting. In hydrogenation reactions, this results in desirably lower reaction temperatures and pressures.

Lower concentrations of such homogeneous catalysts, as compared to heterogeneous systems, may be effectively employed without adversely affecting reaction rates. This reduces the need or incentive for recovery of spent catalyst, since it may be more efficient to include the catalyst in the polymer or copolymer matrix. In addition, because of the small size of the catalyst particles in homogeneous systems, the mechanical properties of the hydrogenated polymer or copolymer are usually not adversely affected by inclusion of the catalyst.

U.S. Pat. Nos. 4,816,525 and 4,812,528 describe a umber of ruthenium carbonyl complexes that may be used in homogeneous organic solution as catalysts for selective hydrogenation of conjugated diene copolymers. U.S. Pat. No. 4,746,707 shows a different set of ruthenium complex catalysts and is directed specifically to hydrogenation of carbon-carbon bonds without concurrent hydrogenation of nonolefin functionality such as nitrile groups.

Other homogeneous catalyst systems using ruthenium, rhodium and other metals are described in U.S. Pat. Nos. 3,898,208, 4,464,515, 4,581,417, 4,795,788, 4,816,525, 4,746,707 and 4,812,528. Each of the systems described in those patents relates to a soluble complex of the metal used for hydrogenation of olefinic unsaturation in diene polymers and copolymers.

In view of the considerations of raw material costs, catalyst recovery costs, catalyst fabrication costs, and reaction constraints, such catalysts systems are rejected in favor of those based upon palladium or its salts.

A homogeneous catalyst system of a palladium salt of a carboxylic acid, e.g., palladium acetate, is described in U.S. Pat. No. 4,510,293. There, the catalyst and polymer are dissolved in a suitable solvent under a pressurized hydrogen atmosphere to selectively hydrogenate the olefinic unsaturation in nitrile rubber (NBR) without reduction of the carbon-nitrogen bonds.

U.S. Pat. No. 4,452,950 describes the homogeneous catalysis of an unsaturated rubber in latex form using various metal ions or salts which may be reduced by hydrazine present in the reaction mixture.

SUMMARY OF THE INVENTION

The present invention is directed to 'homogeneous' colloidal palladium (O) catalyst systems formed by reduction of palladium (II) complexes which are derived from palladium chloride or hydrated palladium oxide, for the hydrogenation of olefinic unsaturation in diene polymers and copolymers including specifically nitrile rubber. More specifically, the invention is directed to the palladium (II) complexes which are the precursors of such catalysts.

According to the present invention, a catalyst precursor is provided that is useful in the hydrogenation of olefinic unsaturation in polymers or copolymers. The precursor comprises a palladium salt complexed with a complexing agent selected from the group consisting of organic phosphates; dialkylidene acetones; and, tetra-alkyl ammonium hydroxides. The complex is stabilized with an organic stabilizing agent to retard metal agglomeration, selected from a group consisting of organic cyanides, ethers, polyethers, organophosphines and organoarsines. It is then combined in solution with an olefinically unsaturated polymer or copolymer under a hydrogen atmosphere at sufficient temperature and pressure to accomplish the desired degree of hydrogenation of the polymer or copolymer.

It is thus an object of the invention to provide "homogeneous" colloidal palladium (O) catalysts which form in situ when the precursor complexes are reduced by hydrogen during hydrogenation of diene polymers and copolymers. It is also an object of the invention to provide colloidal palladium (O) catalysts having the improved characteristics associated with homogeneous catalysis.

It is a further object of the invention to provide a process for producing such catalyst precursor complexes.

Another object of the invention is to provide a continuous process for using the catalyst to hydrogenate olefinically unsaturated polymers or copolymers.

Still another object of the invention is the production of a hydrogenated polymer or copolymer using the aforementioned catalyst complexes.

These and other objects and advantages of the present invention will become apparent from the detailed description of the invention provided below.

DETAILED DESCRIPTION OF THE INVENTION

The catalysts of the present invention are colloidal palladium (O) formed from palladium (II) complexes derived from palladium salts such as palladium chloride and hydrated palladium oxide. The catalysts are used to selectively hydrogenate olefinic uasaturation of dissolved diene polymers and copolymers without concurrent reduction of nonolefinic functionalities such as carbon-nitrogen bonds. The catalysts of the present invention desirably operate in an essentially homogeneous system with the dissolved polymer or copolymer.

The catalysts of the present invention have shown particular utility in the hydrogenation of NBR, which is a copolymer of acrylonitrile and butadiene. More specifically, hydrogenation of fifty to ninety percent and greater has been achieved using the catalysts of the present invention, resulting in the desired oil, sour gas, and ozone resistance not found in the unhydrogenated rubber. Inclusion of these catalysts in the final rubber matrix has not been shown to have an adverse effect on the mechanical properties of the NBR.

In addition to nitrile rubber, the catalysts of the present invention are believed to be useful in the hydrogenation of polybutadiene, polyisoprene, styrene butadiene rubber, butadiene methacrylonitrile rubber, isoprene methacrylonitrile rubber, butadiene isoprene copolymer, butadiene isobutylene copolymer and natural rubber. Copolymers having the following compositions may also be hydrogenated according the present invention:

where:
A is butadiene
B is acrylonitrile or methacrylonitrile and,
C is itaconic acid, fumaric acid, maleic acid, methacrylic acid, acrylic acid, crotonic acid, methytacrylate, ethylacrylate, ethylhexylacrylate, methylmethacrylate, vinyl pyridine or vinyl acetate.

A third group of copolymers which may be hydrogenated using the catalysts of the present invention are those having the structure DE, DED or DEFED, where D is butadiene, E is styrene or alpha-methylstyrene, and F is a coupling residue.

The active forms of palladium (O) are generated from palladium (II) complexes derived from palladium (II) salts. These catalyst precursors are derivatives of various complexing agents, including organo phosphates, aryl-substituted alpha, beta unsaturated ketones or tetra-alkyl ammonium hydroxides.

The first of such catalyst precursor complexes is a palladium organo phosphate derived from an organic phosphoric acid. These organo phosphates may be mono- or di-substituted, having respectively the structures I and II shown below. Such complexes may be mixtures of different monosubstituted organo phosphates, mixtures of different di-substituted organo phosphates, or mixtures of mono- and di- substituted organo phosphates.

Monosubstituted organo phosphates useful in the present invention have the structure:

wherein $R_1$ is alkyl, aryl, aralkyl, cycloalkyl, or any physical mixture of these types of phosphoric acids. Suitable alkyl groups include methyl, ethyl, n-propyl, isopropyl, n-butyl, isobutyl, sec-butyl, and similar groups. Aryl groups include phenyl, benzo, naphthyl, indenyl and similar groups. Useful aralkyl groups include benzyl, tolyl, xylyl, and the like, while cycloalkyl groups include cyclopentyl, cyclohehexyl, cycloheptyl, etc.

Useful disubstituted phosphoric acid derivatives have the structure:

wherein $R_1$ and $R_2$ are alkyl, aryl, aralkyl cycloalkyl, or any combination of these types of substituents or any physical mixture of these phosphoric acid derivatives. Alkyl groups include methyl, ethyl, n-propyl, isopropyl, n-butyl, isobutyl, sec-butyl, and similar groups. Aryl groups include phenyl, benzo, naphthyi, indenyl and similar groups. Useful aralkyl groups include benzyl, tolyl, xylyl, and the like, while cycloalkyl groups include cyclopentyl, cyclohexyl, cycloheptyl, etc. $R_1$ and $R_2$ may be the same or different in structure II.

One example of such a composition is bisacetonitrile palladium phenylphosphate. This complex is formed from a solution of palladium chloride in hydrochloric acid. Aqueous sodium hydroxide is added to produce a gelatinous red-brown precipitate of hydrated palladium oxide, which is removed by filtering and washed with water and acetonitrile (MeCN). This solid precipitate is extracted repeatedly with an acetonitrile solution containing phenylphosphoric acid to dissolve as much of the solid as possible. Finally, excess acetonitrile is stripped off under pressure. The resulting catalyst precursor is a yellow-orange oil, which may be added to a solution containing the diene polymer or copolymer.

A second and related catalyst precursor uses bisacetonitrile complexed with an alkyl phosphate, for example, a mixture of mono- and di- isopropylphosphate or mono- or di- (n-butyl) phosphate. The precursor is formed from an aqueous solution of palladium chloride containing sodium chloride, to produce a solution of sodium tetrachloropalladium (II). Sodium carbonate is added to this solution to produce a red-brown precipitate of hydrated palladium oxide. The washed solids are then mixed with acetonitrile to produce a slurry, to which the phosphate, e.g., a mixture of mono- and di-isopropylphosphoric acid or di(n-butyl) phosphoric acid, is added to form a catalyst precursor. This mixture is sonicated to dissolve the resulting hydrated palladium oxide, and the excess acetonitrile is stripped off to leave a yellow-orange oil. This oil may be added to a solution containing the diene polymer or copolymer.

A second catalyst precursor is formed by complexlug palladium with a dialkylidene acetone having the structure III of a 1,4-pentadiene-3-one derivative:

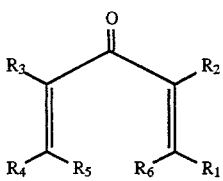

wherein $R_1$ to $R_6$ may be the same or different, and are hydrogen, alkyl, aryl, aralkyl, or cycloalkyl. Suitable alkyl groups include methyl, ethyl, n-propyl, isopropyl, n-butyl, isobutyl, sec-butyl, and similar groups. Aryl groups include phenyl, benzo, naphthyl, indenyl and similar groups. Useful aralkyl groups include benzyl, beta-phenethyl, etc., while cycloalkyl groups include cyclopentyl, cyclohexyl, cycloheptyl, and the like.

Other ligands which contain the pentadiene-3-one structure are derivatives of 4-(methylene)-2,5-cyclohexadiene-1-one and cyclopentadieneone:

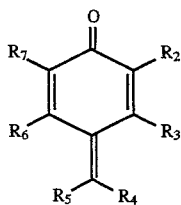

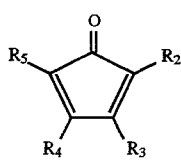

wherein $R_2$–$R_7$ for the 4-(methylene)-2,5-cyclohexadiene-1-one derivatives and $R_2$–$R_5$ for the cylcopentadieneone derivatives may be the same or different, and are hydrogen, alkyl, aryl, aralkyl, or cycloalkyl groups. Suitable alkyl groups include methyl, ethyl, n-propyl, isopropyl, n-butyl, isobutyi, sec-butyl, and similar groups. Aryl groups include phenyl, benzo, naphthyl, indenyl and similar groups. Useful aralkyl groups include benzyl, beta-phenethyl groups, etc., and the like.

An example of such a catalyst complex has the structure $Pd_2DBA3.CHCl_3$, in which DBA is dibenzylideneacetone. This complex is formed by the addition of palladium (II) chloride to a methanol solution containing sodium acetate and dibenzylideneacetone. The reaction mixture was warmed to 55° C. for one hour to form a precipitate, noting that excessive heating causes decomposition of the complex to palladium metal. The precipitate and catalyst precursor is filtered from the methanol and redissolved in chloroform to produce a dark purple solution, which is stripped under reduced pressure to produce a dark purple-black solid of $Pd_2DBA3.CHCl_3$. This solid is redissolved and added to a solution of diene polymer or copolymer.

The fourth related catalyst precursor complex of the present invention is tetrabutylammonium hydroxide/bisacetonitrile palladium (II) chloride. This catalyst is synthesized from either of two reaction schemes. A methanol solution of tetrabutylammonium hydroxide is prepared, and the methanol stripped off under reduced pressure. Acetonitrile is added to the resulting clear oil, and solvent once again stripped. A solution of palladium chloride in acetonitrile is added to the tetrabutylammonium hydroxide solution to produce a deep red solution, from which the acetonitrile is stripped. The resulting oil is dissolved in acetone, which may then be combined with an acetone or other solution of the diene polymer or copolymer.

An alternative method of synthesizing the fourth catalyst complex is obtained by dissolving palladium chloride in acetonitrile along with tetrabutylammonium chloride, producing a red solution. Pulverized sodium hydroxide is added and stirred for approximately 18 hours. The solution is then filtered and the solvent stripped off under reduced pressure. The resulting red oil is dissolved in acetone, which may then be combined with an acetone or other solution of the diene polymer or copolymer.

Besides tetrabutylammonium hydroxide, other tetra-alkyl ammonium hydroxides may be successfully employed. Preferably, such compounds have from $C_1$ to $C_6$ alkyl groups.

In these complexes, acetonitrile and tetrahydrofuran are employed as stabilizers to stabilize the catalyst when formed. Other stabilizing agents, such as polyethers, organophosphines, or organoarsines may also be successfully employed in the present invention to prevent crystallization or precipitation of the catalyst.

Each of the foregoing colloidal catalyst precursor complexes is effective to hydrogenate olefinic unsaturation in diene polymers and copolymers. This is shown by the examples below.

EXAMPLE I 0.49 g palladium chloride were dissolved in 9 g distilled water containing 0.31 g HCl, and the resulting solution was heated to between 60° and 80° C., and then allowed to cool to room temperature. 0.66 g sodium hydroxide was dissolved in 9 g distilled water, which was then added to the palladium chloride solution to produce a gelatinous precipitate. The precipitate was removed by gravity filtration through a fritted funnel, and washed with 50–80 mL warm water, followed by 50 mL acetonitrile, to produce a solid residue of hydrated palladium oxide. The residue was extracted four times with 50 mL acetonitrile solution containing 1.12 g phenylphosphoric acid. (Additional phosphoric acid (0.45 g) was unsuccessfully employed to dissolve the remaining residue.) The acetonitrile was stripped off under reduced pressure to leave 2.43 g of a yellow-orange oil. The oil was then dissolved in 100 mL tetrahydrofuran (TEF), and the catalyst solution was charged to a pressure vessel containing an NBR having 29–31wt % acrylonitrile dissolved in 1.1–1.3 L TEF. After 22 hours at 75°–85° C. and 350 psi hydrogen, a cast film of the reaction mixture indicated that 70 percent of the olefinic NBR unsaturation had been hydrogenated.

EXAMPLE II 1.05 g palladium chloride were added to a 100 mL methanol solution containing 3.9 g sodium acetate and 4.6 g dibenzylideneacetone. The reaction mixture was warmed to 55° C. and the temperature maintained for one hour so that a precipitate was formed. The precipitate was then filtered from the methanol and redissolved in chloroform to produce a dark purple solution. This solution was stripped under reduced pressure at 25°–30° C. to produce a dark purple or black solid of $Pd_2DBA3.CHCl_3$. 1.5 g of the solid was dissolved in 100 mL THF, and added to a solution of 140–150 g of 30–5 NBR in 1.1–1.2 L THF. After 22 hours at 75°–90° C. and 350 psi hydrogen, a sample was withdrawn and a cast film IR analysis indicated that 63 percent of the olefinic NBR unsaturation had been hydrogenated.

EXAMPLE III 4 mL of a 1M methanol solution of tetrabutylammonium hydroxide was placed in a flask, and the methanol stripped off under reduced pressure. 30 mL acetonitrile was added to the resulting clear oil and the solution stripped again. A separate solution of 0.50 g palladium chloride in 100 mL acetonitrile was prepared and added to the tetrabutylammonium hydroxide residue to produce a deep red solution. Acetonitrile was stripped from this reaction mixture and the deep red oil product was redissolved in acetone (100 mL). This palladium solution was added to a solution of 140–150 g 30–5 NBR in 1.1–1.2 L acetone. After 21.5 hours at 66°–78° C. and 375–390 psi hydrogen, an IR analysis of the reaction mixture indicated that 66 percent of the olefinic NBR unsaturation had been hydrogenated.

EXAMPLE IV 0.5 g palladium chloride was dissolved in 100 mL acetonitrile with 1.11 g tetrabutylammonium chloride, producing a red solution. 0.16–0.2 g pulverized sodium hydroxide was added to the solution, and the reaction mixture stirred for about 18 hours. The solution was filtered and solvent stripped off under reduced pressure to produce a red oil. 1.7 g of the red oil was redissolved in acetone and added to a solution containing 140–150 g 30–5 NBR in 1.1–1.2 L acetone. After 22.5 hours at 66°–81° C. and 355–360 psi hydrogen, an IR analysis of the reaction mixture indicated that 41 percent of the olefinic NBR had been hydrogenated.

In general, it has been found that catalyst complexes prepared from approximately 0.5 g palladium chloride per 140 g NBR in 1–1.2 L of solvent are effective to achieve 60–70 percent hydrogenation in 20–24 hours at 200–350 psi and 50°–120° C. It has been shown that even higher yields of hydrogenated polymer or copolymer may be achieved by optimizing the temperature, pressure, solvent, and mount of catalyst employed.

Upon obtaining the desired hydrogenation, the unreacted hydrogen may be vented, or the pressure otherwise reduced, to terminate the hydrogenation reaction. Alternatively, the palladium catalyst may be coagulated by heating the polymer/catalyst solution to a sufficiently high temperature to cause the particles of palladium (O) to agglomerate into larger particles, or to precipitate onto larger particles, thereby reducing catalyst activity.

Numerous catalyst and polymer solvents are useful in the practice of the present invention; most useful are those in which both the polymer or copolymer to be hydrogenated and the catalyst are soluble, and are typically low molecular weight ketones, especially acetone and methyl ethyl ketone (MEK). Other useful solvents include benzene, toluene, xylene, hexane, cyclohexane, tetrahydrofuran and ethylacetate. Those skilled in the art will appreciate that other solvents may also be usefully employed in the present invention without adversely affecting the performance of the catalysts described herein.

In general, the catalysts of the present reaction may be used to hydrogenate polymers and copolymers under a wide range of reaction conditions; the specific reaction conditions chosen will depend upon the specific catalyst employed, the polymers or copolymers being hydrogenated, the desired rate of reaction, and other variables recognized by those skilled in the art. The catalysts are operable under 150–1000 psi, with pressures greater than 400 psi being likely to improve catalyst performance and hydrogenation yield. Reaction temperatures ranging from 20°–120° C., and preferably from 60°–90° C., are useful. Appropriate reaction times range from 4–20 hours, and will depend upon the other reaction variables chosen and the desired amount of hydrogenation.

The catalysts of the present invention may be used to achieve hydrogenation yields of sixty to ninety percent, or even more, of the olefinic unsaturation in NBR. Since it is possible to obtain hydrogenation yields of sixty to ninety percent of the olefinic unsaturation in nitrile rubber without significant hydrogenation of the carbon-nitrogen bonds, the desirable environmental resistance characteristics are achieved along with an increase in the service temperature of the copolymer.

In addition, because the catalysts of the present invention are in essentially the same phase as the dissolved polymer or copolymer, the step of removing catalyst from the system may preferably be avoided. This results in substantial cost savings as compared to heterogeneous catalyst systems. In addition, homogeneous catalysis enables hydrogenation of the polymer or copolymer in a continuous system while avoiding the undesirable generation of a catalyst waste stream.

It has also been found that the step-wise and continuous additions of catalyst result in a reduction in time necessary to achieve the desired amount of hydrogenation. Thus, it has been found desirable to add the catalyst to the dissolved polymer or copolymer in at least two stages, and an alternative continuous addition process has also been shown to be effective. The continuous addition process is also desirable because it permits large-scale continuous processing of the diene copolymer and avoids the problems of batch processes known to those skilled in the art.

Step-wise and continuous addition processes are illustrated by Examples V and VI.

EXAMPLE V 0.8 g palladium chloride were dissolved in 15 g distilled water containing 0.61 g sodium chloride. The mixture was heated to 60°–80° C. until the palladium chloride was completely dissolved, approximately one-half hour, producing a solution of sodium tetrachloropalladium (II). A solution of 1.18 g sodium carbonate in 15 g distilled water was added to the sodium tetrachloropalladium (II) solution after the latter had been cooled in an ice/water bath of one-half hour. This produced a red-brown gelatinous precipitate, which was isolated by centrifuging and decanting the aqueous layer. The solids were washed with distilled water, and the damp solids transferred to an Erlenmeyer flask with 100 mL acetonitrile to produce a slurry. A mixture of 42.4 wt. percent mono- and 53.6 wt. percent di- isopropylphosphoric acid (1.73 g) was added to the acetonitrile slurry, and the resulting mixture sonicated for one hour to solubilize the hydrated palladium oxide. The acetonitrile was stripped off under reduced pressure to leave 2.81 g of a yellow orange oil, which was dissolved in 90 g MEK. 45 g of this solution was charged to a pressure vessel containing 206 g 33-NBR (33 wt. percent acrylonitrile, 67 wt. percent butadiene) dissolved in 1.1–1.3 L MEK. After 115 min. at 60°–62° C. and 203–205 psi hydrogen flowing at 145–160 mL/min., a cast film of the reaction mixture indicated that 46.6 percent of the olefinic NBR unsaturation had been hydrogenated. Addition of the remaining catalyst solution, and continued hydrogenation under the same conditions for three more hours resulted in an overall hydrogenation yield of 88 percent.

EXAMPLE VI 0.8 g palladium chloride were dissolved in 17 g distilled water containing 0.55 g sodium chloride. The mixture was heated to 60°–80° C. until the palladium chloride was completely dissolved, approximately one-half hour, producing a solution of sodium tetrachloropalladium (II). A solution of 1.03 g sodium carbonate in 12 g distilled water was added to the sodium tetrachloropalladium (II) solution after the latter had been cooled in an ice/water bath of one-half hour. This produced a red-brown gelatinous precipitate, which was isolated by centrifuging and decanting the aqueous layer. The solids were washed with distilled water, and the damp solids transferred to an erlenmeyer flask with 100 mL acetonitrile to produce a slurry. A mixture of 42.4 wt. percent mono- and 53.6 wt. percent di- isopropylphosphoric acid (1.57 g) was added to the acetonitrile slurry, and the resulting mixture sonicated for one hour to solubilize the hydrated palladium oxide. The acetonitrile was stripped off under reduced pressure to leave 2.5 g of a yellow orange oil, which was dissolved in 250 mL MEK. A mini pump was used to add 1.1 mL/min. of this solution to a pressure vessel containing 200 g 33-NBR dissolved in 1250 g MEK. Hydrogen was added to the vessel at 190-200 psi and 150-160 mL/min. at 43°-53° C. After 120 min., the catalyst addition was stopped, and a cast film of the reaction mixture indicated that 30-32 percent of the olefinic NBR unsaturation had been hydrogenated. No change in the amount of hydrogenation was observed at three hours. The addition of the catalyst solution was restarred, and continued hydrogenation resulted in an overall hydrogenation yield of 84 percent after six hours and 86.5 percent after 6.5 hours.

Other examples of continuously added catalyst are set forth in Table I.

TABLE I

Experimental conditions for hydrogenation of 30-NBR using palladium phosphate catalyst precursors (rate of addition = 1 mL/min.)

| Amount NBR (g) | Amount MEK (g) | Amount PdCl$_2$/ Acid | Temp. (°C.) | H$_2$ Press. (psi) | H$_2$ flow (mL/min.) | time (hrs) | Yield (%) |
|---|---|---|---|---|---|---|---|
| 250 | 1391 | 0.8/ 1.32[1,3] | 43-53 | 195-210 | 130-170 | 5 | 89 |
| 250 | 1389 | 0.8/ 1.58[2,3] | 46-53 | 195-200 | 143-158 | 6.25 | 89 |
| 235 | 1365 | 0.8/ 1.57[2,3] | 41-53 | 200-205 | 135-160 | 6.33 | 91.3 |
| 255 | 1379 | 0.8/ 1.58[2,4] | 48-52 | 360-365 | 150-170 | 6 | 89.1 |

[1]The acid was a mixture of 42.4 wt % mono- and 53.6 wt % di- isopropyl phosphoric acid.
[2]The acid was a mixture of 38.4 wt % mono- and 61.7 wt % di- (n-butyl) phosphoric acid.
[3]Volume of catalyst solution in (25 vol %) MeCN/MEK was 250 mL.
[4]Volume of catalyst solution in MeCN was 250 mL.

Of the palladium phosphate catalyst precursors described herein, the catalyst precursor formed by complexing hydrated palladium oxide with di(n-butyl) phosphoric acid is preferred. Table II shows data pertaining to the use of that precursor in a continuous addition system, and indicates that yield is governed principally by amounts of active catalyst in the system, rather than hydrogen pressure or other variables.

TABLE II

Hydrogenation of 30-NBR with palladium phosphate catalyst precursor formed from di(n-butyl) phosphoric acid (rate of catalyst addition = 1 mL/min.)

| Amount NBR (g) | Amount MEK (g) | Amount PdCl$_2$/ Acid | Temp. (°C.) | H$_2$ Press. (psi) | H$_2$ flow (mL/min.) | time (hrs) | Yield (%) |
|---|---|---|---|---|---|---|---|
| 255 | 1385 | 0.8/ 1.92[1,2] | 41-53 | 200-204 | 145-160 | 6 | 93.2 |
| 260 | 1350 | 0.8/ 1.88[1,2] | 47-58 | 195-200 | 150-160 | 6.25 | 92.4 |
| 255 | 1393 | 0.4/ 0.955[1,3] | 42-50 | 200-210 | 147-160 | 5.1 | 47.6 |
| 255 | 1411 | 0.4/ 0.955[1,3] | 42-50 | 360-365 | 150-180 | 5.9 | 50.2 |

[1]The acid was di(n-butyl) phosphoric acid.
[2]The volume of catalyst solution in MeCN was 250 mL.
[3]The volume of catalyst solution in MeCN was 127 mL.

The present invention has been described with respect to certain embodiments and conditions, which are not meant to and should not be construed to limit the invention. Those skilled in the art will understand that variations from the embodiments and conditions described herein may be made without departing from the invention as claimed in the appended claims.

What is claimed is:

1. A catalyst precursor for use in the hydrogenation of olefinic unsaturation in polymers and copolymers prepared in an organic solvent at a temperature low enough to avoid decomposition of the catalyst precursor comprising the reaction product of (a) a palladium (II) chloride salt with (b) a tetraalkyl ammonium hydroxide complexing agent and (c) an organic stabilizing agent to retard metal agglomeration selected from the group consisting of organic cyanides, organic ethers and organic polyethers.

2. A catalyst precursor as defined in claim 1 wherein the stabilizing agent is selected from the group consisting of acetonitrile and tetrahydrofuran.

3. The catalyst precursor of claim 1, wherein said tetraalkyl ammonium hydroxide is tetrabutylammonium hydroxide.

* * * * *